United States Patent
Amanai et al.

(10) Patent No.: US 10,488,635 B2
(45) Date of Patent: Nov. 26, 2019

(54) IMAGE PICKUP APPARATUS

(71) Applicant: OLYMPUS CORPORATION, Hachioji-shi, Tokyo (JP)

(72) Inventors: Takahiro Amanai, Hachioji (JP); Kyoko Iijima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 45 days.

(21) Appl. No.: 15/953,764

(22) Filed: Apr. 16, 2018

(65) Prior Publication Data
US 2018/0307010 A1   Oct. 25, 2018

(30) Foreign Application Priority Data

Apr. 20, 2017 (JP) ................................ 2017-083368

(51) Int. Cl.
| | |
|---|---|
| G02B 13/18 | (2006.01) |
| G02B 13/04 | (2006.01) |
| G02B 9/12 | (2006.01) |
| G02B 13/00 | (2006.01) |
| G02B 13/06 | (2006.01) |
| G02B 23/24 | (2006.01) |
| A61B 1/00 | (2006.01) |
| A61B 1/04 | (2006.01) |

(52) U.S. Cl.
CPC .......... G02B 13/04 (2013.01); A61B 1/00096 (2013.01); A61B 1/00188 (2013.01); G02B 9/12 (2013.01); G02B 13/0035 (2013.01); G02B 13/06 (2013.01); G02B 23/243 (2013.01); G02B 23/2469 (2013.01); *A61B 1/041* (2013.01)

(58) Field of Classification Search
CPC .... G02B 13/04; G02B 13/06; G02B 23/2469; G02B 23/243; G02B 9/12; G02B 13/0035
See application file for complete search history.

(56) References Cited

U.S. PATENT DOCUMENTS 9,459,431 B2   10/2016  Hirose
2014/0139711 A1*   5/2014  Sano ..................... G02B 13/18
348/294

FOREIGN PATENT DOCUMENTS

JP   2013025202 A   2/2013
WO   2012090729 A1   7/2012

* cited by examiner

*Primary Examiner* — Joseph P Martinez
(74) *Attorney, Agent, or Firm* — Holtz, Holtz & Volek PC

(57) ABSTRACT

An image pickup apparatus includes an image forming optical system which includes an aperture stop and a plurality of lens components, and an image pickup section which is disposed on an image side of the image forming optical system, and has a light-receiving surface which is not flat and is curved to be concave toward the image forming optical system. The image forming optical system includes a first lens component having a negative refractive power, a second lens component having a positive refractive power, and a third lens component having a positive refractive power. A shape of the first lens component is a meniscus shape, and a shape of the third lens component is a biconvex shape, and the following conditional expressions (1) and (2) are satisfied:

$0.7 < |PS \times Rimg| < 1.5$     (1), and $0.7 < |\theta out\ 90 / \theta img\ 90| < 1.5$     (2).

8 Claims, 9 Drawing Sheets

IMAGE PICKUP APPARATUS

CROSS-REFERENCE TO RELATED APPLICATION

The present application is based upon and claims the benefit of priority from the prior Japanese Patent Application No. 2017-083368 filed on Apr. 20, 2017; the entire contents of which are incorporated herein by reference.

BACKGROUND OF THE INVENTION

Field of the Invention

The present invention relates to an image pickup apparatus.

Description of the Related Art

An optical system having a wide angle of view, which forms a curved image, has been disclosed in Japanese Patent Application Laid-open Publication No. 2013-025202 (example 6) and International Unexamined Patent Application Publication No. 2012/090729 (example 4).

In the Japanese Patent Application Laid-open Publication No. 2013-025202 and International Unexamined Patent Application Publication No. 2012/090729, an optical system which includes a first lens component having a negative refractive power, a second lens component having a positive refractive power, and a third lens component having a positive refractive power has been disclosed. In this optical system, an image plane is curved.

SUMMARY OF THE INVENTION

An image pickup apparatus according to at least some of the embodiments of the present invention, comprises:

an image forming optical system which includes an aperture stop that determines an axial light beam, and a plurality of lens components, and an image pickup section which is disposed on an image side of the image forming optical system, and has a light-receiving surface which is not flat and is curved to be concave toward the image forming optical system, wherein the lens component is a lens having only two surfaces in contact with air on an optical axis, which are an object-side surface and an image-side surface, and the image forming optical system includes in order from an object side to an image side, a first lens component having a negative refractive power, a second lens component having a positive refractive power, and a third lens component having a positive refractive power, and a shape of the first lens component is a meniscus shape having a convex surface directed toward the object side, and a shape of the third lens component is a biconvex shape, and the following conditional expressions (1) and (2) are satisfied:

$$0.7 < |PS \times Rimg| < 1.5 \quad (1), \text{ and}$$

$$0.7 < |\theta out\, 90 / \theta img 90| < 1.5 \quad (2)$$

where,

PS denotes Petzval sum for the image forming optical system, and

Petzval sum PS is expressed by the following expression:

$$PS = \sum_{i=1}^{k} \frac{1}{n_i \times f_i}$$

where, i denotes an order of lens components from the object side in the image forming optical system, k denotes the total number of lens components in the image forming optical system, $n_i$ denotes a refractive index of an $i^{th}$ lens component for d-line, $f_i$ denotes a focal length of the $i^{th}$ lens component for d-line, Rimg denotes a radius of curvature of a virtual spherical surface including a surface apex and a point at which a chief ray incident on the image forming optical system at the maximum angle of view intersects the light-receiving surface, letting a point of intersection of the optical axis and the image-receiving surface to be the apex, θout 90 denotes an angle made by a predetermined chief ray emerged from an image-side surface of the third lens component and the optical axis, θimg 90 denotes an angle made by a straight line passing through two predetermined points and the optical axis, the predetermined chief ray is a chief ray for which an angle made with the optical axis becomes 90°, in a space on the object side of the first lens component, and the two predetermined points are a point of intersection of the predetermined chief ray emerged from the image-side surface of the third lens component and the virtual surface, and a center of curvature of the virtual surface.

DETAILED DESCRIPTION OF THE INVENTION

Figure 1A:
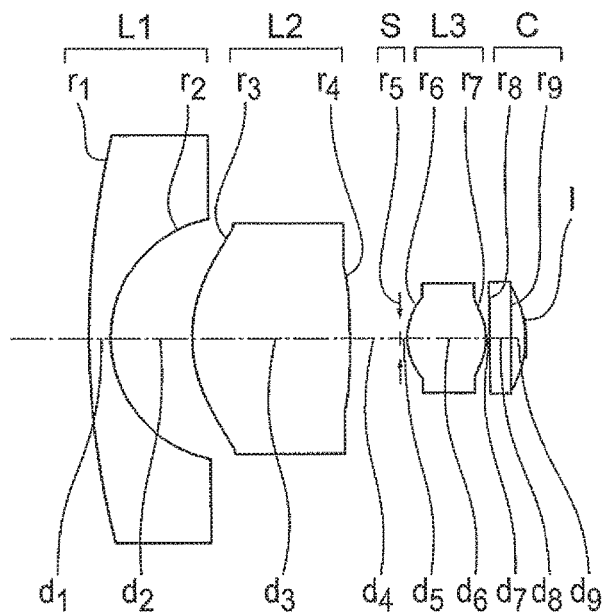
FIG. 1A, and FIG. 1B, FIG. 1C, FIG. 1D, and FIG. 1E are a cross-sectional view and aberration diagrams respectively, of an image forming optical system according to an example 1.
Figures 1B, 1C, 1D, 1E:
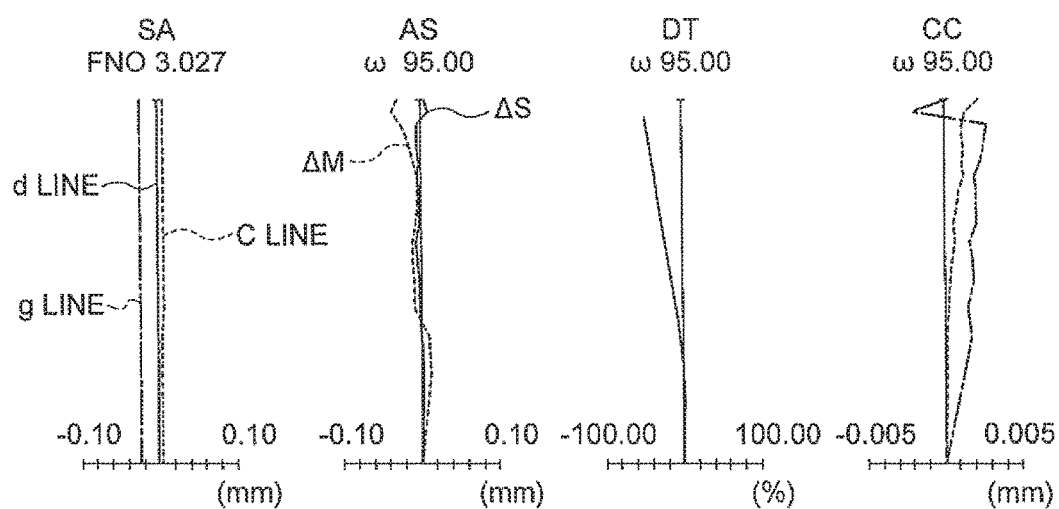
Figure 2A:
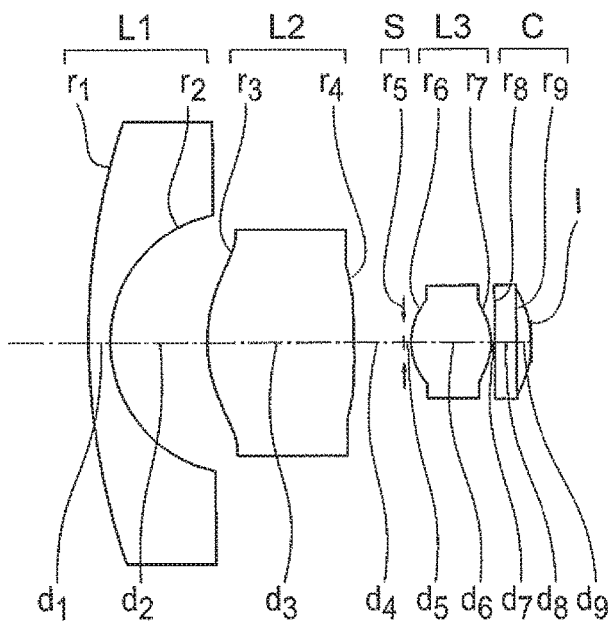
FIG. 2A, and FIG. 2B, FIG. 2C, FIG. 2D, and FIG. 2E are a cross-sectional view and aberration diagrams respectively, of an image forming optical system according to an example 2.
Figures 2B, 2C, 2D, 2E:
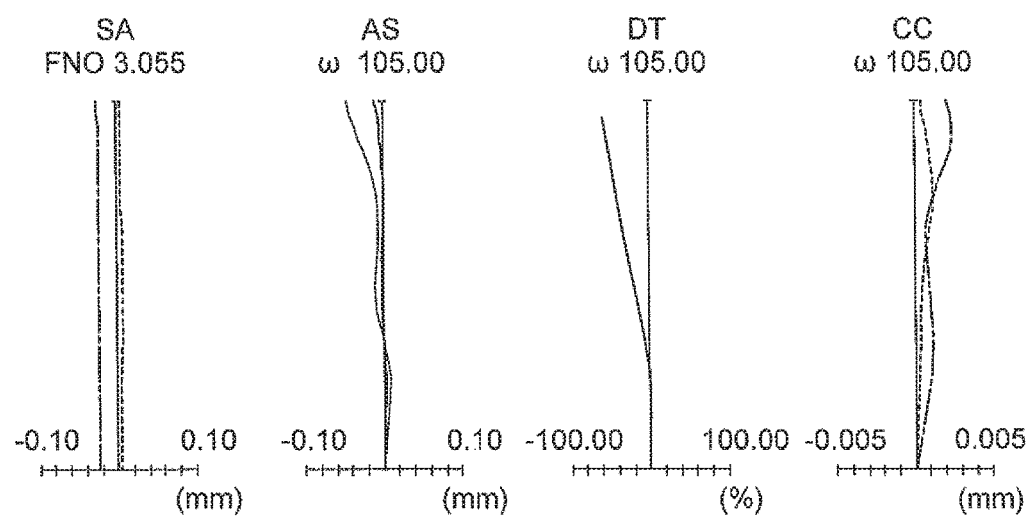
Figure 3A:
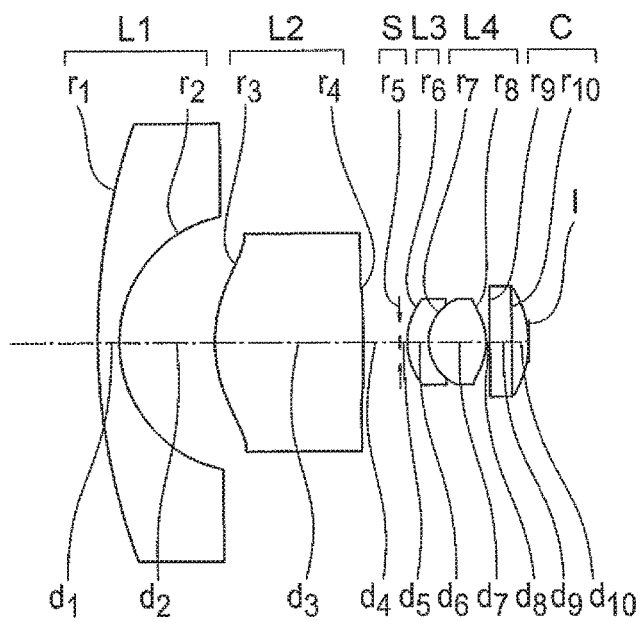
FIG. 3A, and FIG. 3B, FIG. 3C, FIG. 3D, and FIG. 3E are a cross-sectional view and aberration diagrams respectively, of an image forming optical system according to an example 3.
Figures 3B, 3C, 3D, 3E:
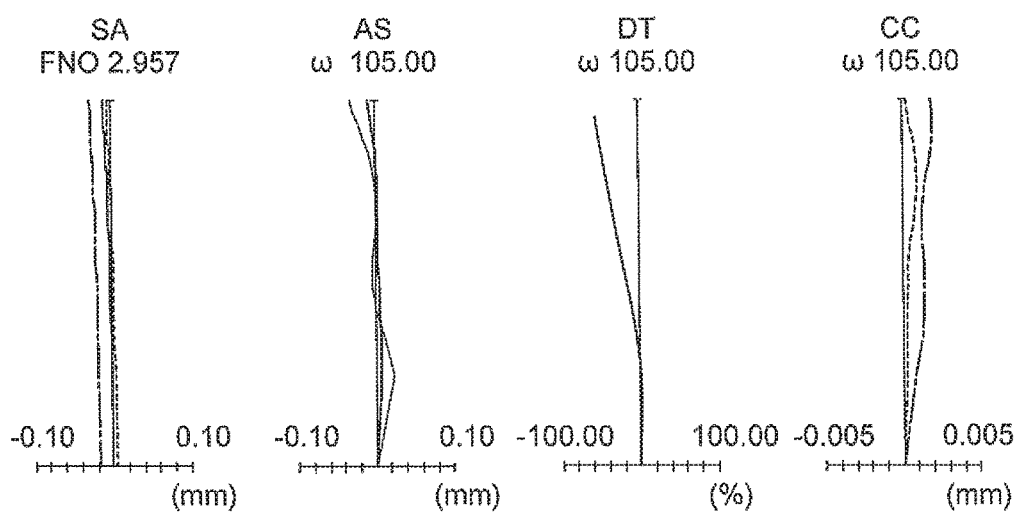
Figure 4A:
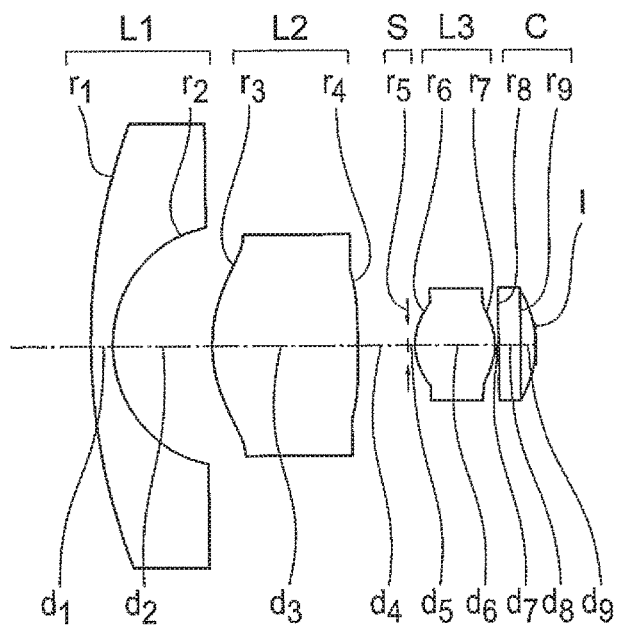
FIG. 4A, and FIG. 4B, FIG. 4C, FIG. 4D, and FIG. 4E are a cross-sectional view and aberration diagrams respectively, of an image forming optical system according to an example 4.
Figures 4B, 4C, 4D, 4E:
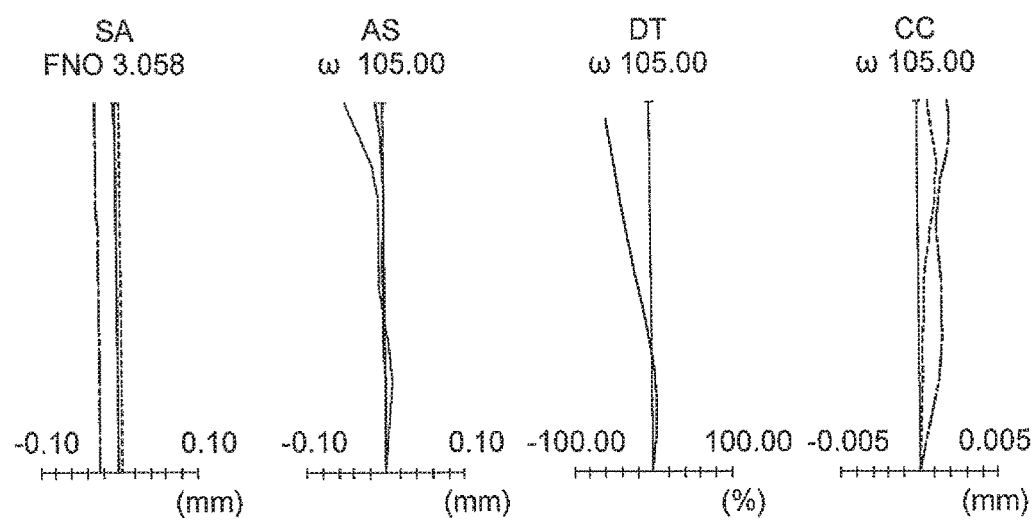

Prior to describing the examples, an action and an effect of an embodiment according to certain aspects of the present invention will be described below. For describing specifically the action and the effect of the present embodiment, the description will be made by citing concrete examples. Similar to a case of examples to be described later, the aspects to be exemplified are some of the aspects of the present invention, and there exist a large number of variations of these aspects. Therefore, the present invention is not limited to the aspects that are exemplified.

An image pickup apparatus of the present embodiment includes an image forming optical system which includes an aperture stop that determines an axial light beam, and a plurality of lens components, and an image pickup section which is disposed on an image side of the image forming optical system, and has a light-receiving surface which is not flat and is curved to be concave toward the image forming optical system, wherein the lens component is a lens having only two surfaces in contact with air on an optical axis, which are an object-side surface and an image-side surface, and the image forming optical system includes in order from an object side to an image side, a first lens component having a negative refractive power, a second lens component having a positive refractive power, and a third lens component having a positive refractive power, and a shape of the first lens component is a meniscus shape having a convex surface directed toward the object side, and a shape of the third lens component is a biconvex shape, and the following conditional expressions (1) and (2) are satisfied:

$$0.7 < |PS \times Rimg| < 1.5 \quad (1), \text{ and}$$

$$0.7 < |\theta out\ 90/\theta img 90| < 1.5 \quad (2)$$

where,

PS denotes Petzval sum for the image forming optical system, and

Petzval sum PS is expressed by the following expression:

$$PS = \sum_{i=1}^{k} \frac{1}{n_i \times f_i}$$

where, i denotes an order of lens components from the object side in the image forming optical system, k denotes the total number of lens components in the image forming optical system, $n_i$ denotes a refractive index of an $i^{th}$ lens component for d-line, $f_i$ denotes a focal length of the $i^{th}$ lens component for d-line, Rimg denotes a radius of curvature of a virtual spherical surface including a surface apex and a point at which a chief ray incident on the image forming optical system at the maximum angle of view intersects the light-receiving surface, letting a point of intersection of the optical axis and the image-receiving surface to be the apex, θout 90 denotes an angle made by a predetermined chief ray emerged from an image-side surface of the third lens component and the optical axis, θimg 90 denotes an angle made by a straight line passing through two predetermined points and the optical axis, the predetermined chief ray is a chief ray for which an angle made with the optical axis becomes 90°, in a space on the object side of the first lens component, and the two predetermined points are a point of intersection of the predetermined chief ray emerged from the image-side surface of the third lens component and the virtual surface, and a center of curvature of the virtual surface.

The image pickup apparatus of the present embodiment, while being small-sized, is capable of capturing a wide photographing range with a high resolution. Therefore, in the image pickup apparatus of the present embodiment, the image forming optical system used in the image pickup apparatus, while being small-sized, is made to have a wide angle of view and a small F-number, and also, is arranged such that a favorable image can be formed. A favorable image refers to an optical image in which aberrations from a central portion up to a peripheral portion are corrected favorably.

In the image pickup apparatus of the present embodiment, the image forming optical system includes the aperture stop and the plurality of lens components. The aperture stop is a stop that determines an axial light beam. The lens component is a lens having only two surfaces in contact with air on the optical axis, which are the object-side surface and the image-side surface.

As mentioned above, the lens component has the object-side surface and the image-side surface as the surfaces in contact with air. In the following description, the object-side surface out of the two surfaces in contact with air islet to be a lens surface on the object side. The lens surface on the object side is positioned nearest to object in the lens component. Moreover, the image-side surface out of the two surfaces in contact with air is let to be a lens surface on the image side. The lens surface on the image side is positioned nearest to image in the lens component.

The image pickup section is disposed on the image side of the image forming optical system. The image pickup section has the light-receiving surface which is not flat, but is curved to be concave toward the image forming optical system. An image formed on the light-receiving surface is curved to be concave toward the object side.

In an optical system which forms an image which is completely or partially curved to be concave toward the object side (hereinafter, referred to as 'curved image'), an occurrence of a curvature of field to certain extent is acceptable. Therefore, in the optical system which forms a curved image, a load of aberration correction is reduced as compared to a load in an optical system which forms a flat image.

For instance, in an optical system which forms a curved image, it is possible to reduce a lens for correcting Petzval sum. Consequently, it is possible to make the optical system small in size.

Moreover, in an optical system which forms a flat image, for correcting the curvature of field favorably, it is necessary to dispose a lens for correction at a position away from an aperture stop. However, when the lens for correction is disposed, an outer diameter of the optical system becomes large, and furthermore, the number of lens components increases. Thus, the lens for correction is one of the causes that make the outer diameter of the optical system large.

Whereas, in an optical system that forms a curved image, it is not necessary to dispose the lens for correction. Consequently, in an optical system that forms a curved image, it is possible to make the outer diameter of the optical system small.

Moreover, a relative illumination, or in other words, a ratio of an amount of light in a central area to an amount of light in a peripheral area, is suppressed from being degraded. Moreover, further occurrence of distortion is suppressed.

Furthermore, for receiving an image of an optical system by an image sensor having a curved image pickup surface, the optical system may not be let to be a telecentric optical system for making a light ray incident on the image pickup surface to be almost perpendicular. Consequently, in an optical system that forms a curved image, a degree of freedom of a design in order to achieve both of downsizing and optical performance, is widened.

The image forming optical system in the image pickup apparatus of the present embodiment is also an optical system which forms a curved image. Consequently, it is possible to reduce the number of lens components and to make the optical system small-sized. Furthermore, since the degree of freedom of a design is widened, it is possible to realize an optical system having a high imaging performance while securing a wide angle of view such as 180 degrees or more.

In the image pickup apparatus of the present embodiment, the image forming optical system includes in order from the object side to the image side, the first lens component having a negative refractive power, the second lens component having a positive refractive power, and the third lens component having a positive refractive power. By making such arrangement, even being the image forming optical system having a wide angle of view and a small F-number, it is possible to secure a favorable imaging performance. Moreover, since the image forming optical system becomes small-sized, it is possible to make the image pickup apparatus small-sized.

The first lens component has a negative refractive power. By making such arrangement, it is possible to secure a favorable imaging performance from a central portion up to a peripheral portion of the photographing range even when the angle of view is 180 degrees or more.

The shape of the first lens component is a meniscus shape having the convex surface directed toward the object side. Accordingly, it is possible to make small an angle formed by a light ray incident on a lens surface on the object side and a normal of the lens surface. As a result, it is possible to suppress an occurrence of a coma, an occurrence of an astigmatism, and an occurrence of a distortion.

Light incident on the third lens component is refracted at the third lens component. At this time, when the light is refracted in a diverging direction, a spherical aberration and the coma are more susceptible to occur.

The third lens component has a positive refractive power. Moreover, the shape of the third lens component is a biconvex shape. By making such arrangement, it is possible to make the light incident on the third lens component to be refracted in a converging direction. As a result, it is possible to suppress an occurrence of spherical aberration and an occurrence of coma.

In such manner, in the image forming optical system in the image pickup apparatus of the present embodiment, a lens component of a meniscus shape having the convex surface directed toward the object side is used for the first lens element having a negative refractive power, and a lens component of a biconvex shape is used for the third lens component having a positive refractive power. Consequently, even when the image forming optical system is let to be a bright optical system with a wide angle of view, it is possible to secure a favorable imaging performance from a central portion up to a peripheral portion of an imaging range. A bright optical system with a wide angle of view is an optical system having a wide angle of view and a small F-number, and, for example, is an optical system having the F-number not more than 3.5 and the angle of view not less than 180 degrees.

By arranging the image forming optical system such that a value satisfies the conditional expression (1), it is possible to make an amount of curvature of a curvature of field occurring in the image forming optical system almost same as an amount of curvature of the light-receiving surface. Consequently, it is possible to suppress an effect of the curvature of field. As a result, it is possible to make the image forming optical system of the image pickup apparatus a bright optical system with a wide angle of view. Moreover, it is possible to realize an image pickup apparatus which is small-sized, and is capable of acquiring an image having a high image quality.

In a case where the value does not satisfy the conditional expression (1), a difference in the amount of curvature of the curvature of field occurring in the image forming optical system and the amount of curvature of the light-receiving surface becomes excessively large. Consequently, an effect of the curvature of field becomes large. As a result, degradation of an image quality occurs in an image achieved by capturing.

For suppressing the effect of the curvature of field, it is necessary to increase the number of lenses for example. In this case, it becomes difficult to arrange a bright optical system with a wide angle of view by three lens components.

By arranging the image forming optical system such that a value satisfies the conditional expression (2), for a chief ray of each image height, it is possible to make a curvature in a meridional direction and a curvature in a sagittal direction almost coincide. Consequently, it is possible to make the image forming optical system of the image pickup apparatus a bright optical system with a wide angle of view. Moreover, it is possible to realize an image pickup apparatus which is small-sized, and is capable of acquiring an image having a high image quality.

In a case where the value does not satisfy the conditional expression (2), for the chief ray of each image height, the difference in the curvature of the meridional direction and the curvature of the sagittal direction becomes excessively large. Consequently, an amount of the astigmatism that occurs becomes large.

It is preferable that the following conditional expression (1-1) be satisfied instead of the conditional expression (1).

$$0.8<|PS \times Rimg|<1.4 \quad (1\text{-}1)$$

It is preferable that the following conditional expression (2-1) be satisfied instead of the conditional expression (2).

$$0.75<|\theta out\ 90/\theta img90|<1.3 \quad (2\text{-}1)$$

It is possible to find a value of θimg 90 from the following expression:

$$\theta img\ 90 = \arcsin\ (IM\ 90/Rimg)$$

where,

IM 90 denotes the shortest length from a point of intersection of a predetermined light ray emerged from an image-side surface of the third lens component and a virtual spherical surface up to the optical axis.

As mentioned above, the lens component has the object-side surface and the image side surface as surfaces in contact with air. Specific examples of the lens component are a single lens and a cemented lens. There are two types of cemented lenses. In a first type of cemented lens, a plurality of lenses is cemented by an adhesive. In a second type of cemented lens, an adhesive is not used and lenses are in direct contact.

In the image pickup apparatus of the present embodiment, it is preferable that the aperture stop be disposed between a lens nearest to image of the second lens component and a lens surface nearest to object of the third lens component.

As a location for disposing the aperture stop, a position between the lens surface nearest to image of the second lens component and the lens surface nearest to object of the third lens component (hereinafter, referred to as 'predetermined position') and a position other than the predetermined position (hereinafter, referred to as 'another position') may be possible. An example of the another position is a position between the lens surface nearest to image of the first lens component and the lens surface nearest to object of the second lens component.

When the aperture stop is disposed at the predetermined position, a lens component having a positive refractive power is disposed each on the object side and the image side of the aperture stop. In other words, the image forming optical system has a portion in which an arrangement of the refractive power is symmetrical about the aperture stop. In this case, when compared to a case in which the aperture stop is disposed at the another position, a balance of the refractive power near the aperture stop becomes relatively favorable. As a result, it is possible to suppress an occurrence of an off-axis aberration, and particularly an occurrence of the chromatic aberration of magnification.

As light passed through the aperture stop is refracted in the diverging direction, the spherical aberration and the coma are more susceptible to occur. The third lens component is positioned on the image side of the aperture stop. As mentioned above, the third lens component has a positive refractive power. Therefore, at the third lens component, it is possible to refract a light ray passed through the aperture stop in the converging direction. As a result, it is possible to suppress an occurrence of spherical aberration and an occurrence of coma.

A position of the aperture stop may be on a lens surface nearest to image of the second lens component or on a lens surface nearest to object of the third lens component.

In the image pickup apparatus of the present embodiment, it is preferable that the following conditional expression (3) be satisfied:

$$0.5<fL3/fL<3.4 \qquad (3)$$

where, fL3 denotes a focal length of the third lens component, and fL denotes a focal length of the image forming optical system.

As mentioned above, in the third lens component, the refractive power is a positive refractive power and the shape is a biconvex shape. By satisfying the conditional expression (3) in the third lens component having such refractive power and shape, even when the image forming optical system is let to be a bright optical system with a wide angle of view, it is possible to form a favorable image.

By making an arrangement such that a value does not fall below a lower limit value of the conditional expression (3), it is possible secure the brightness of the optical system adequately while suppressing an amount of the spherical aberration that occurs and an amount of the coma that occurs. Securing adequately the brightness of the optical system signifies that it is possible to make the F-number of the optical system adequately small.

By making an arrangement such that the value does not exceed an upper limit value of the conditional expression (3), it is possible to not let the angle of view to be excessively small.

It is more preferable that the following conditional expression (3-1) be satisfied instead of the conditional expression (3).

$$0.5<fL3/fL<3 \qquad (3\text{-}1)$$

In the image pickup apparatus of the present embodiment, it is preferable that the following conditional expression (4) be satisfied:

$$1<(R1L+R1R)/(R1L-R1R)<2.5 \qquad (4)$$

where,

R1L denotes a paraxial radius of curvature of a lens surface nearest to object of the first lens component, and R1R denotes a paraxial radius of curvature of a lens surface nearest to image of the first lens component.

As mentioned above, in the first lens component, the refractive power is a negative refractive power, and the shape is a meniscus shape having a convex surface directed toward the object side. By satisfying the conditional expression (4) in the first lens component having such refractive power and shape, even when the image forming optical system is let to be a bright optical system with a wide angle of view, it is possible to form a favorable image.

In a case where a value does not satisfy the conditional expression (4), the negative refractive power of the first lens component becomes excessively small. Consequently, with a wide angle of view such as the full angle of view of 180 degrees and more, it becomes difficult to form a favorable image.

It is more preferable that the following conditional expression (4-1) be satisfied instead of the conditional expression (4).

$$1<(R1L+R1R)/(R1L-R1R)<1.75 \qquad (4\text{-}1)$$

In the image pickup apparatus of the present embodiment, it is preferable that the following conditional expression (5) be satisfied:

$$-2<(R2L+R2R)/(R2L-R2R)<0 \qquad (5)$$

where,

R2L denotes a paraxial radius of curvature of a lens surface nearest to object of the second lens component, and R2R denotes a paraxial radius of curvature of a lens surface nearest to image of the second lens component.

When the shape of the lens surface nearest to object of the second lens component is let to be a shape having a convex surface directed toward the object side, it is possible to suppress an occurrence of astigmatism. When the lens surface nearest to image of the second lens component is let to be a shape having a convex surface directed toward the object side, it is possible to suppress an occurrence of astigmatism. When the lens surface nearest to image of the second lens component is let to be a shape having a convex surface directed toward the image side, it is possible to suppress an occurrence of spherical aberration and occurrence of coma.

In such manner, the lens surface nearest to object of the second lens component and the lens surface nearest to image of the second lens component contribute to the occurrence of spherical aberration, the occurrence of coma, and the occurrence of astigmatism.

By satisfying the conditional expression (5), the radius of curvature of the lens surface nearest to image of the second lens component becomes larger than the radius of curvature of the lens surface nearest to object of the second lens component. As a result, it is possible to suppress the occurrence of spherical aberration, the occurrence of coma, and the occurrence of astigmatism in a balanced manner. A comparison of the radii of curvature is a comparison in absolute values.

Particularly, in the second lens component, the refractive power is a positive refractive power. By satisfying the conditional expression (5) for the second lens component having such refractive power, it is possible to suppress the occurrence of spherical aberration, the occurrence of coma, and the occurrence of astigmatism.

In a case where ae value does not satisfy the conditional expression (5), when compared in the absolute values, the radius of curvature of the lens surface nearest to image of the second lens component becomes excessively small. Consequently, it becomes difficult to suppress the occurrence of spherical aberration, the occurrence of coma, and the occurrence of astigmatism in a balanced manner.

As mentioned above, it is possible to position the aperture stop on the lens surface nearest to image of the second lens component or on the lens surface nearest to object of the third lens component. When the conditional expression (5) is satisfied in such state, it is possible to suppress more effectively, the occurrence of spherical aberration, the occurrence of coma, and the occurrence of astigmatism.

It is more preferable that the following conditional expression (5-1) be satisfied instead of the conditional expression (5).

$$-1.5<(R2L+R2R)/(R2L-R2R)<-0.7 \quad (5\text{-}1)$$

In the image pickup apparatus of the present embodiment, it is preferable that the following conditional expression (6) be satisfied:

$$2.5<fL2/fL<8 \quad (6)$$

Where, fL2 denotes a focal length of the second lens component, and fL denotes the focal length of the image forming optical system.

When the refractive power of the second lens component becomes excessively large, it becomes difficult to secure a wide angle of view. By satisfying the conditional expression (6), even when the image forming optical system is let to be a bright optical system with a wide angle of view, it is possible to form a favorable image.

By making an arrangement such that a value does not fall below a lower limit value of the conditional expression (6), it is possible to secure a wide angle of view, and moreover, it is possible to not let the coma and the astigmatism to be corrected excessively. By making an arrangement such that the value does not exceed an upper limit value of the conditional expression (6), it is possible to not let the coma and the astigmatism be corrected inadequately.

It is more preferable that the following conditional expression (6-1) be satisfied instead of the conditional expression (6).

$$3.5<fL2/fL<6.5 \quad (6\text{-}1)$$

In the image pickup apparatus of the present embodiment, it is preferable that each of the second lens component and the third lens component have an aspherical surface.

In the second lens component and the third lens component, it is preferable to let the lens surface nearest to object to be an aspherical surface, or to let the lens surface nearest to image to be an aspherical surface, or to let both the surfaces to be aspherical surfaces.

By making such arrangement, it is possible to suppress the occurrence of spherical aberration, the occurrence of coma, and the occurrence of astigmatism.

In the first lens component, it is possible to let both surfaces to be spherical surfaces. However, an aspherical surface may be used in the first lens component. In this case, it is preferable to let a lens surface nearest to object of the first lens component to be a spherical surface, and a lens surface nearest to image of the first lens component to be an aspherical surface. It is also possible to let the lens surface nearest to object of the first lens component to be an aspherical surface.

In the image pickup apparatus of the present embodiment, it is preferable that each of the first lens component, the second lens component, and the third lens component be a single lens.

By making such arrangement, it is possible to make the optical system further small-sized.

It is preferable that the image pickup apparatus of the present embodiment further include an illuminating section, and a cover portion which is disposed on the object side of the image forming optical system.

By disposing the cover portion, it is possible to make an arrangement such that a distance between an object and the image forming optical system is not close excessively, and it is useful for letting the object to be within a depth of field. By including the illuminating section, it becomes useful for night photography and intracavitary photography.

In the image pickup apparatus of the present embodiment, it is preferable that the cover portion be a cover portion having a dome shape covering both of the image forming optical system and the illuminating section.

By making such arrangement, it is possible to make an arrangement such that a distance between the object and the illuminating section is not excessively close, and to reduce an overexposure of a photographic image.

It is preferable that the image pickup apparatus of the present embodiment include the image pickup apparatus, the illuminating section, and the cover portion having a dome shape which is disposed on the object side of the image forming optical system and the illuminating section.

The image pickup apparatus of each embodiment is advantageous for downsizing. Therefore, by providing the illuminating section and the cover portion having a dome shape, it is possible to use the image pickup apparatus as a capsule endoscope.

Examples of the image forming optical system to be used in the image pickup apparatus (hereinafter, referred to as 'image forming optical system') and examples of the image pickup apparatus will be described below by referring to the accompanying diagrams. However, the present invention is not restricted to the examples described below.

Cross-sectional views will be described below. FIG. 1A, FIG. 2A, FIG. 3A, and FIG. 4A show lens cross-sectional views.

Aberration diagrams will be described below.

FIG. 1B, FIG. 2B, FIG. 3B, and FIG. 4B show a spherical aberration (SA).

FIG. 1C, FIG. 2C, FIG. 3C, and FIG. 4C show an astigmatism.

FIG. 1D, FIG. 2D, FIG. 3D, and FIG. 4D show a distortion.

FIG. 1E, FIG. 2E, FIG. 3E, and FIG. 4E show a chromatic aberration of magnification.

The astigmatism shows an amount of aberration from a curved light-receiving surface (image pickup surface).

Regarding the distortion, calculation is made by using a stereographic projection method. In the stereographic projection method, an ideal image height Y is indicated by the following expression (A):

$$Y = 2 \times f \times \tan(\omega/2) \quad (A)$$

where,

Y denotes an ideal image height in the stereographic projection method, f denotes a focal length, and ω denotes a half angle of view.

Consequently, it is possible to calculate the distortion from the following expression (B), by using the ideal image height Y and an actual image height y.

$$DT(\%) = (y-Y)/Y \times 100 \quad (B)$$

An image forming optical system of an example 1 includes in order from an object side, a negative meniscus lens L1 having a convex surface directed toward the object side, a biconvex positive lens L2, and a biconvex positive lens L3.

An aperture stop S is disposed between the biconvex positive lens L2 and the biconvex positive lens L3.

An aspherical surface is provided to a total of four surfaces which are, both side surfaces of the biconvex positive lens L2 and both side surfaces of the biconvex positive lens L3.

An image forming optical system of an example 2 includes in order from an object side, a negative meniscus lens L1 having a convex surface directed toward the object side, a biconvex positive lens L2, and a biconvex positive lens L3.

An aperture stop S is disposed between the biconvex positive lens L2 and the biconvex positive lens L3.

An aspherical surface is provided to a total of four surfaces which are, both side surfaces of the biconvex positive lens L2 and both side surfaces of the biconvex positive lens L3.

An image forming optical system of an example 3 includes in order from an object side, a negative meniscus lens L1 having a convex surface directed toward the object side, a positive meniscus lens L2 having a convex surface directed toward the object side, a negative meniscus lens L3 having a convex surface directed toward the object side, and a biconvex positive lens L4. Here, the negative meniscus lens L3 and the biconvex positive lens L4 are cemented.

An aperture stop S is disposed between the positive meniscus lens L2 and the negative meniscus lens L3.

An aspherical surface is provided to a total of four surfaces which are, both side surfaces of the positive meniscus lens L2, an object-side surface of the negative meniscus lens L3, and an image-side surface of the biconvex positive lens L4.

An image forming optical system of an example 4 includes in order from an object side, a negative meniscus lens L1 having a convex surface directed toward the object side, a biconvex positive lens L2, and a biconvex positive lens L3.

An aperture stop S is disposed between the biconvex positive lens L2 and the biconvex positive lens L3.

An aspherical surface is provided to a total of five surfaces which are, an image-side surface of the negative meniscus lens L1, both side surfaces of the biconvex positive lens L2, and both side surfaces of the biconvex positive lens L3.

Figure 5:
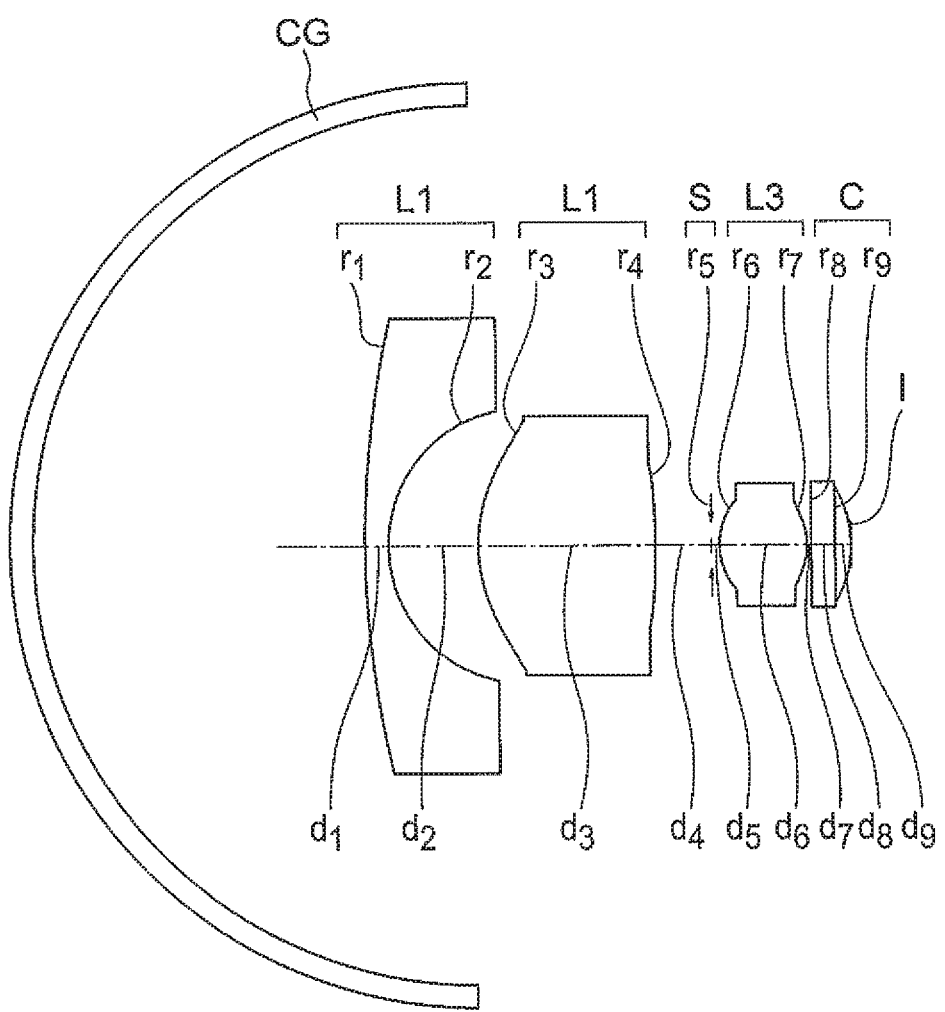
FIG. 5 is a cross-sectional view of an image forming optical system according to an example 5.

An image forming optical system according to an example 5, as shown in FIG. 5, includes in order from an object side, an optical member CG, a negative meniscus lens L1 having a convex surface directed toward the object side, a biconvex positive lens L2, and a biconvex positive lens L3. The optical system including the negative meniscus lens L1, the biconvex positive lens L2, an aperture stop S, and the biconvex positive lens L3 is same as the optical system according to the example 1.

FIG. 5 is a schematic diagram illustrating that the optical member CG can be disposed. Therefore, a size and a position of the optical member CG have not been depicted accurately with respect to sizes and positions of the lenses.

The optical member CG is a member in the form of a plate, and both an object-side surface and an image-side surface thereof are curved surfaces. In FIG. 5, both the object-side surface and the image-side surface being curved surfaces, an overall shape of the optical member CG is hemispherical. In the example 5, a thickness of the optical member CG, or in other words, a distance between the object-side surface and the image-side surface, is constant. However, the thickness of the optical member CG may not be constant.

Moreover, as it will be described later, the optical member CG is disposed at a position only 6.0 mm away on the object side from the object-side surface of the first lens. However, the optical member CG may be disposed at a position shifted frontward or rearward from the abovementioned position. Moreover, a radius of curvature and the thickness of the optical member CG mentioned here is an example, and are not limited to the radius of curvature and the thickness mentioned here.

A material that allows light to transmit through has been used for the optical member CG. Consequently, light from an object passes through the optical member CG and is incident on the negative meniscus lens L1. The optical member CG is disposed such that a curvature center of the image-side surface substantially coincides with a position of an entrance pupil. Consequently, a new aberration due to the optical member CG hardly occurs. In other words, an imaging performance of the image forming optical system according to the example 5 is not different from an imaging performance of the image forming optical system according to the example 1.

The optical member CG functions as a cover glass. In this case, the optical member CG corresponds to an observation window provided at an outer covering of a capsule endoscope. Therefore, the image forming optical system according to the example 5 can be used for an optical system of a capsule endoscope. The image forming optical systems according to the example 1 to the example 4 can also be used for an optical system of an endoscope.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, * denotes an aspherical surface, and stop denotes an aperture stop.

Further, in Various data, f denotes a focal length of the entire system, FNO. denotes an F number, ω denotes a half angle of view, IH denotes an image height, LTL denotes a lens total length of the optical system. The lens total length is a distance from a frontmost lens surface to the rearmost lens surface plus back focus. The back focus is a distance which is expressed upon air conversion of a distance from a rearmost lens surface to a paraxial image surface.

Moreover, the example 5 is an example in which, the optical member CG is disposed on the object side of the image forming optical system according to the example 1. In surface data of the example 5, C1 denotes the object-side surface of the optical member CG and C2 denotes the image-side surface of the optical member CG. Aspherical surface data and various data of the example 5 being same as the aspherical surface data and various data of the example 1, description thereof is omitted here.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'e-n' (where, n is an integral number) indicates '$10^{-n}$'. Moreover, these symbols are commonly used in the following numerical data for each example.

Example 1

Unit mm

Surface data

| Surface no. | r | d | nd | vd |
|---|---|---|---|---|
| 1 | 12.000 | 0.30 | 1.88300 | 40.76 |
| 2 | 1.727 | 1.13 | | |
| 3* | 2.028 | 2.21 | 1.61441 | 25.11 |
| 4* | −21.498 | 0.71 | | |
| 5 (Stop) | ∞ | 0.10 | | |
| 6* | 0.797 | 1.10 | 1.52550 | 55.20 |
| 7* | −0.656 | 0.05 | | |
| 8 | ∞ | 0.30 | 1.51633 | 64.14 |
| 9 | ∞ | 0.20 | | |
| 10 (Image plane) | −1.419 | | | |

Aspherical surface data

3rd surface k = 0.000
A4 = 1.23130e−02, A6 = −1.91427e−02, A8 = 1.49350e−03

4th surface k = 0.000
A4 = −6.38357e−02, A6 = 1.53933e−02

6th surface k = 0.000
A4 = −4.10690e−01, A6 = 5.39893e−01

7th surface k = 0.000
A4 = 2.18638e+00, A6 = −7.75462e+00, A8 = 1.82742e+01

Various data

| f | 0.65 |
|---|---|
| FNO. | 3.03 |
| 2ω | 190.00 |
| IH | 0.73 |
| LTL (in air) | 6.10 |

Example 2

Unit mm

Surface data

| Surface no. | r | d | nd | vd |
|---|---|---|---|---|
| 1 | 9.457 | 0.30 | 1.88300 | 40.76 |
| 2 | 1.812 | 1.34 | | |
| 3* | 2.076 | 2.02 | 1.61441 | 25.11 |
| 4* | −45.362 | 0.69 | | |
| 5 (Stop) | ∞ | 0.10 | | |
| 6* | 0.810 | 1.10 | 1.52550 | 55.20 |
| 7* | −0.676 | 0.05 | | |
| 8 | ∞ | 0.30 | 1.51633 | 64.14 |
| 9 | ∞ | 0.20 | | |
| 10 (Image plane) | −1.433 | | | |

Aspherical surface data

3rd surface k = 0.000
A4 = 9.81846e−03, A6 = −2.04754e−02, A8 = −2.01513e−03

4th surface k = 0.000
A4 = −9.55477e−02, A6 = 2.17816e−02

6th surface k = 0.000
A4 = −4.10206e−01, A6 = 5.88124e−01

7th surface k = 0.000
A4 = 2.22004e+00, A6 = −8.19123e+00, A8 = 1.70592e+01

Various data

| f | 0.67 |
|---|---|
| FNO. | 3.06 |
| 2ω | 210.00 |
| IH | 0.73 |
| LTL (in air) | 6.10 |

Example 3

Unit mm

Surface data

| Surface no. | r | d | nd | vd |
|---|---|---|---|---|
| 1 | 8.900 | 0.30 | 1.88300 | 40.76 |
| 2 | 1.805 | 1.33 | | |
| 3* | 2.059 | 2.06 | 1.61441 | 25.11 |
| 4* | 15.195 | 0.51 | | |
| 5 (Stop) | ∞ | 0.10 | | |
| 6* | 0.894 | 0.30 | 1.68948 | 31.02 |
| 7 | 0.650 | 0.80 | 1.59201 | 67.02 |
| 8* | −0.675 | 0.05 | | |
| 9 | ∞ | 0.30 | 1.51633 | 64.14 |

-continued

Unit mm

| | | | |
|---|---|---|---|
| 10 | ∞ | 0.23 | |
| 11 (Image plane) | −1.426 | | |

Aspherical surface data

3rd surface k = 0.000
A4 = 1.56977e−02, A6 = −2.42074e−02, A8 = −1.25273e−03

4th surface k = 0.000
A4 = −1.60890e−01, A6 = 6.00386e−02

6th surface k = 0.000
A4 = −1.76167e−01, A6 = 7.56171e−02

8th surface k = 0.000
A4 = 2.01450e+00, A6 = −7.30124e+00, A8 = 1.51490e+01

Various data

| | |
|---|---|
| f | 0.63 |
| FNO. | 2.96 |
| 2ω | 210.00 |
| IH | 0.73 |
| LTL (in air) | 5.98 |

Example 4

Unit mm

Surface data

| Surface no. | r | d | nd | vd |
|---|---|---|---|---|
| 1 | 8.610 | 0.30 | 1.88300 | 40.76 |
| 2* | 1.722 | 1.37 | | |
| 3* | 2.034 | 2.00 | 1.61441 | 25.11 |
| 4* | −66.148 | 0.69 | | |
| 5 (Stop) | ∞ | 0.10 | | |
| 6* | 0.804 | 1.10 | 1.52542 | 55.78 |
| 7* | −0.680 | 0.05 | | |
| 8 | ∞ | 0.30 | 1.51633 | 64.14 |
| 9 | ∞ | 0.20 | | |
| 10 (Image plane) | −1.509 | | | |

Aspherical surface data

2nd surface k = 0.061
A4 = −4.38879e−03, A6 = 2.15203e−03

3rd surface k = 0.000
A4 = 1.14398e−02, A6 = −1.99268e−02, A8 = −1.87863e−03

4th surface k = 0.000
A4 = −9.72838e−02, A6 = 2.19605e−02

6th surface k = 0.000
A4 = −3.77500e−01, A6 = 3.96953e−01

7th surface k = 0.000
A4 = 2.23131e+00, A6 = −8.18718e+00, A8 = 1.70915e+01

Various data

| | |
|---|---|
| f | 0.66 |
| FNO. | 3.06 |
| 2ω | 210.00 |
| IH | 0.73 |
| LTL (in air) | 6.10 |

An amount of distortion calculated by using the stereographic projection method is shown below.

Example 1

TABLE 1

| ω [°] | y [mm] | Y [mm] | DT [%] |
|---|---|---|---|
| 0 | 0.00 | 0.00 | 0.0 |
| 10 | 0.11 | 0.11 | 1.0 |
| 20 | 0.23 | 0.23 | 2.1 |
| 30 | 0.35 | 0.35 | −0.2 |
| 40 | 0.44 | 0.47 | −6.2 |
| 50 | 0.52 | 0.60 | −14.0 |
| 60 | 0.58 | 0.75 | −21.9 |
| 70 | 0.64 | 0.90 | −29.4 |
| 80 | 0.69 | 1.08 | −36.8 |
| 95 | 0.73 | 1.41 | −47.9 |

Example 2

TABLE 2

| ω [°] | y [mm] | Y [mm] | DT [%] |
|---|---|---|---|
| 0 | 0.00 | 0.00 | 0.0 |
| 10 | 0.12 | 0.12 | 1.1 |
| 20 | 0.24 | 0.24 | 2.4 |
| 30 | 0.36 | 0.36 | 0.1 |
| 40 | 0.46 | 0.49 | −6.5 |
| 50 | 0.53 | 0.62 | −15.0 |
| 60 | 0.59 | 0.77 | −23.6 |
| 70 | 0.64 | 0.94 | −31.8 |
| 80 | 0.68 | 1.12 | −39.5 |
| 90 | 0.71 | 1.34 | −47.0 |
| 100 | 0.73 | 1.60 | −54.3 |
| 105 | 0.73 | 1.75 | −58.0 |

Example 3

TABLE 3

| ω [°] | y [mm] | Y [mm] | DT [%] |
|---|---|---|---|
| 0 | 0.00 | 0.00 | 0.0 |
| 10 | 0.11 | 0.11 | 1.1 |
| 20 | 0.23 | 0.22 | 2.9 |
| 30 | 0.35 | 0.34 | 1.6 |
| 40 | 0.44 | 0.46 | −3.9 |
| 50 | 0.52 | 0.59 | −11.9 |
| 60 | 0.58 | 0.73 | −20.3 |
| 70 | 0.63 | 0.89 | −28.5 |
| 80 | 0.68 | 1.06 | −36.5 |
| 90 | 0.71 | 1.27 | −44.2 |
| 100 | 0.73 | 1.51 | −51.8 |
| 105 | 0.73 | 1.65 | −55.6 |

Example 4

TABLE 4

| ω [°] | y [mm] | Y [mm] | DT [%] |
|---|---|---|---|
| 0 | 0.00 | 0.00 | 0.0 |
| 10 | 0.12 | 0.11 | 4.9 |
| 20 | 0.24 | 0.22 | 6.5 |
| 30 | 0.35 | 0.34 | 4.2 |
| 40 | 0.45 | 0.46 | −2.9 |
| 50 | 0.52 | 0.59 | −11.9 |
| 60 | 0.58 | 0.73 | −20.9 |
| 70 | 0.63 | 0.89 | −29.3 |
| 80 | 0.67 | 1.06 | −37.1 |
| 90 | 0.70 | 1.27 | −44.6 |
| 100 | 0.73 | 1.51 | −51.9 |
| 105 | 0.73 | 1.65 | −55.6 |

Next, values of conditional expressions in each example are given below.

| Conditional expression | Example 1 | Example 2 |
|---|---|---|
| (1) |PS × Rimg| | 1.32 | 1.32 |
| (2) |θout90/θimg90| | 0.86 | 0.83 |
| (3) fL3/fL | 1.43 | 1.40 |
| (4) (R1L + R1R)/(R1L − R1R) | 1.34 | 1.47 |
| (5) (R2L + R2R)/(R2L − R2R) | −0.83 | −0.91 |
| (6) fL2/fL | 4.80 | 4.86 |

| Conditional expression | Example 3 | Example 4 |
|---|---|---|
| (1) |PS × Rimg| | 1.29 | 1.38 |
| (2) |θout90/θimg90| | 0.79 | 0.88 |
| (3) fL3/fL | 1.41 | 1.43 |
| (4) (R1L + R1R)/(R1L − R1R) | 1.51 | 1.50 |
| (5) (R2L + R2R)/(R2L − R2R) | −1.31 | −0.94 |
| (6) fL2/fL | 5.72 | 4.90 |

Figure 6:
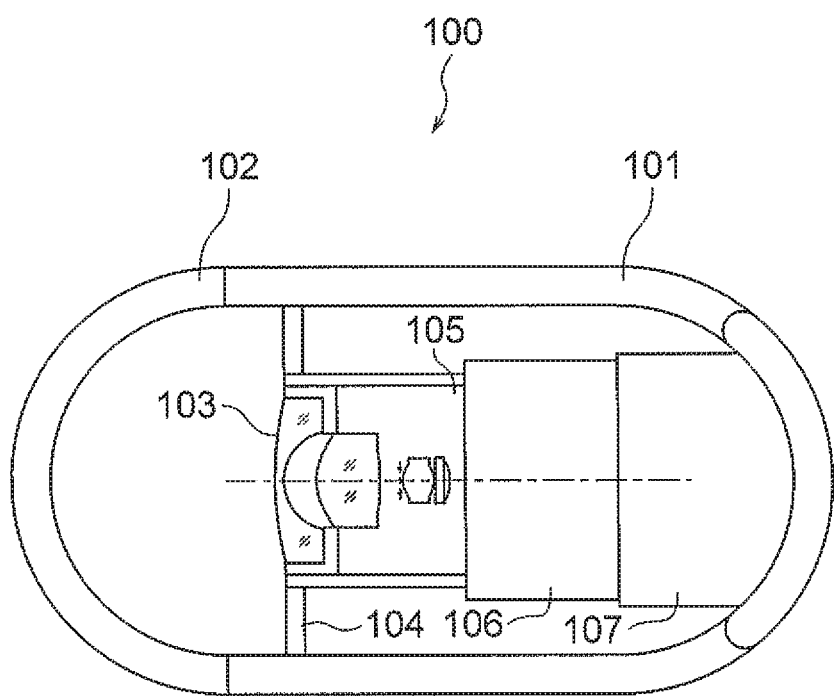
FIG. 6 is a diagram showing a schematic arrangement of a capsule endoscope.

FIG. 6 illustrates an example of an image pickup apparatus. In this example, the image pickup apparatus is a capsule endoscope. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, a illumination unit 104, an image sensor 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image sensor 105. A drive and control of the image sensor 105 is carried out by the drive control unit 106. Moreover, an output signal from the image sensor 105 is processed by the signal processing unit 107 according to the requirement.

Here, for the image forming optical system 103, the image forming optical system according to the abovementioned example 1 for instance, is used. In such manner, the image forming optical system 103 has a wide angle of view and a small F-number, while being small-sized. Consequently, in the image forming optical system 103, a wide-angle optical image having a high resolution is acquired.

Moreover, the capsule endoscope 100 includes an optical system having a wide angle of view and a small F-number while, being small-sized. Consequently, in the capsule endoscope 100, it is possible to acquire a wide-angle image with high resolution, while being small-sized.

Here, the image sensor has a curved light-receiving surface. However, even when the light-receiving surface of the image sensor is flat, if a surface receiving an image is curved, that surface may be referred to as a curved light-receiving surface. As such example, an arrangement in which a fiber bundle is disposed on a light-receiving surface of an image sensor having a flat light-receiving surface, and one end surface thereof is fabricated to be curve-shaped, and an object image is received on this curved surface, may be possible.

Figure 7A:
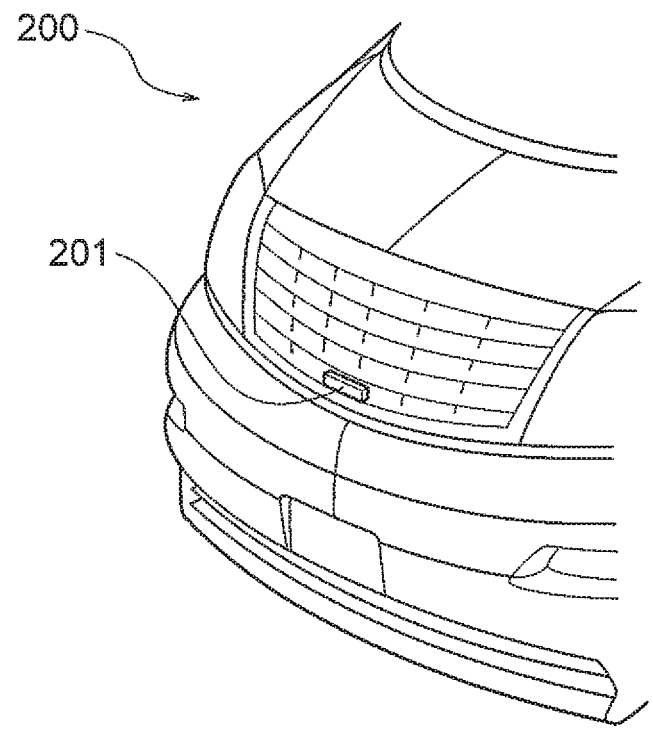
FIG. 7A and FIG. 7B are diagrams showing a car-mounted camera.
Figure 7B:
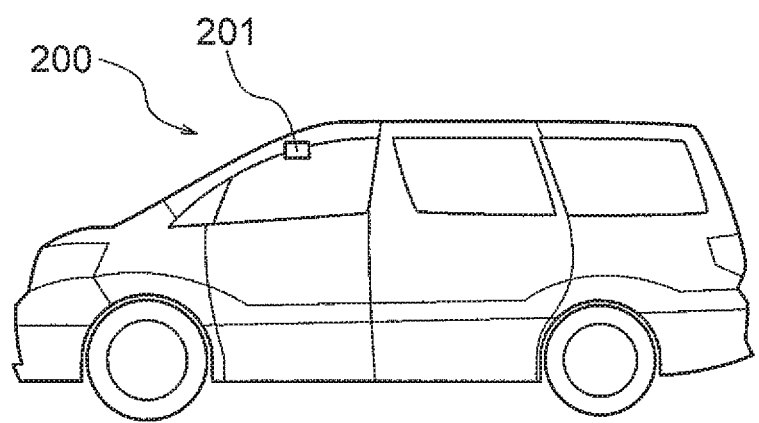

FIG. 7A and FIG. 7B are diagrams illustrating another example of an image pickup apparatus. In this example, the image pickup apparatus is a car-mounted camera. FIG. 7A is a diagram illustrating an example of a car-mounted camera mounted at an outside of a car, and FIG. 7B is a diagram illustrating an example of a car-mounted camera mounted inside a car.

As shown in FIG. 7A, a car-mounted camera 201 is provided to a front grill of an automobile 200. The car-mounted camera 201 includes an image forming optical system and an image sensor. For the image forming optical system of the car-mounted camera 201, the image forming optical system according to the abovementioned example 1 is used. Consequently, a favorable optical image is formed.

As shown in FIG. 7B, the car-mounted camera 201 is provided near a ceiling of the automobile 200. An action and an effect of the car-mounted camera 201 are as have already been described. In the car-mounted camera 201, it is possible to acquire an image with high resolution, while being small-sized.

Figure 8:
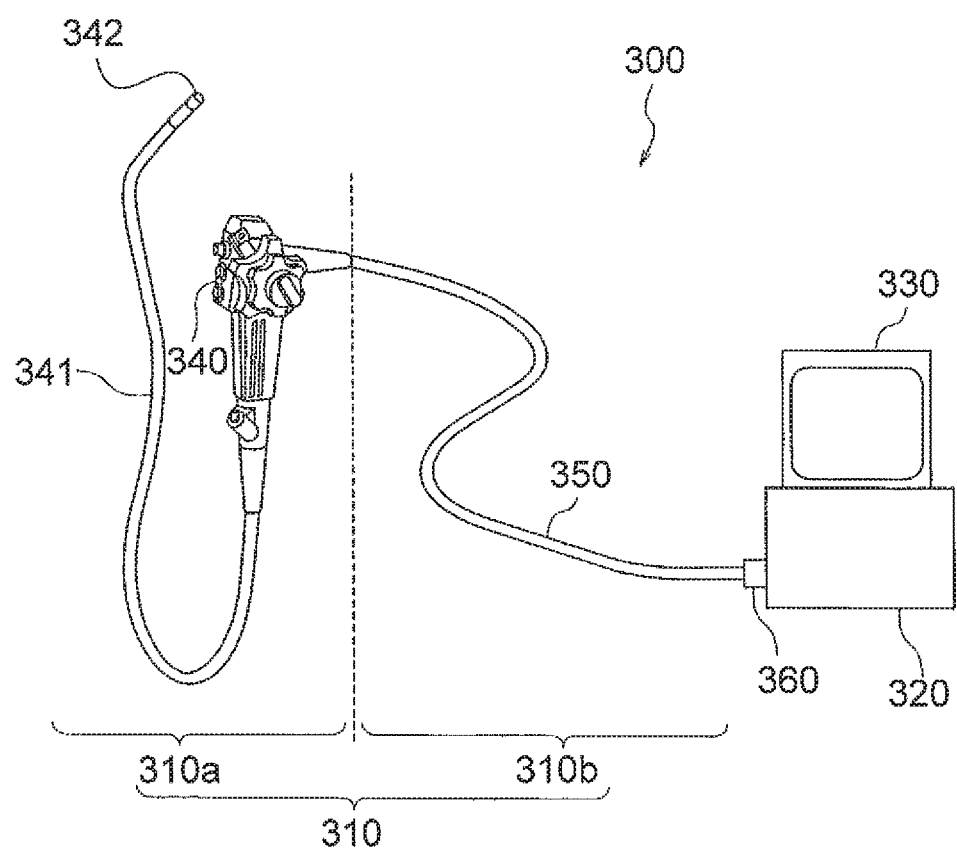
FIG. 8 is a diagram showing a schematic arrangement of an endoscope system.

FIG. 8 is a diagram illustrating another example of an image pickup apparatus. In this example, the image pickup apparatus is an endoscope system. FIG. 8 is a diagram showing a schematic arrangement of the endoscope system.

An endoscope system 300 is an observation system in which an electronic endoscope is used. The endoscope system 300 includes an electronic endoscope 310 and an image processing unit 320. The electronic endoscope 310 includes a scope section 310a and a connecting cord section 310b. Moreover, a display unit 330 is connected to the image processing unit 320.

The scope section 310a is mainly divided into an operating portion 340 and an inserting portion 341. The inserting portion 341 is long and slender, and can be inserted into a body cavity of a patient. Moreover, the inserting portion 341 is formed of a flexible member. An observer can carry out various operations by an angle knob that is provided to the operating portion 340.

Moreover, the connecting cord section 310b is extended from the operating portion 340. The connecting cord section 301b includes a universal cord 350. The universal cord 350 is connected to the image processing unit 320 via a connector 360.

The universal cord 350 is used for transceiving of various types of signals. Various types of signals include signals such as a power-supply voltage signal and a CCD (charge coupled device) driving signal. These signals are transmitted from a power supply unit and a video processor to the scope section 310a. Moreover, various types of signals include a video signal. This signal is transmitted from the scope section 310a to the video processor.

Peripheral equipment such as a VTR (video tape recorder) deck and a video printer can be connected to the video processor inside the image processing unit 320. The video processor carries out signal processing on a video signal from the scope section 310a. On the basis of the video signal, an endoscope image is displayed on a display screen of the display unit 330.

Figure 9:
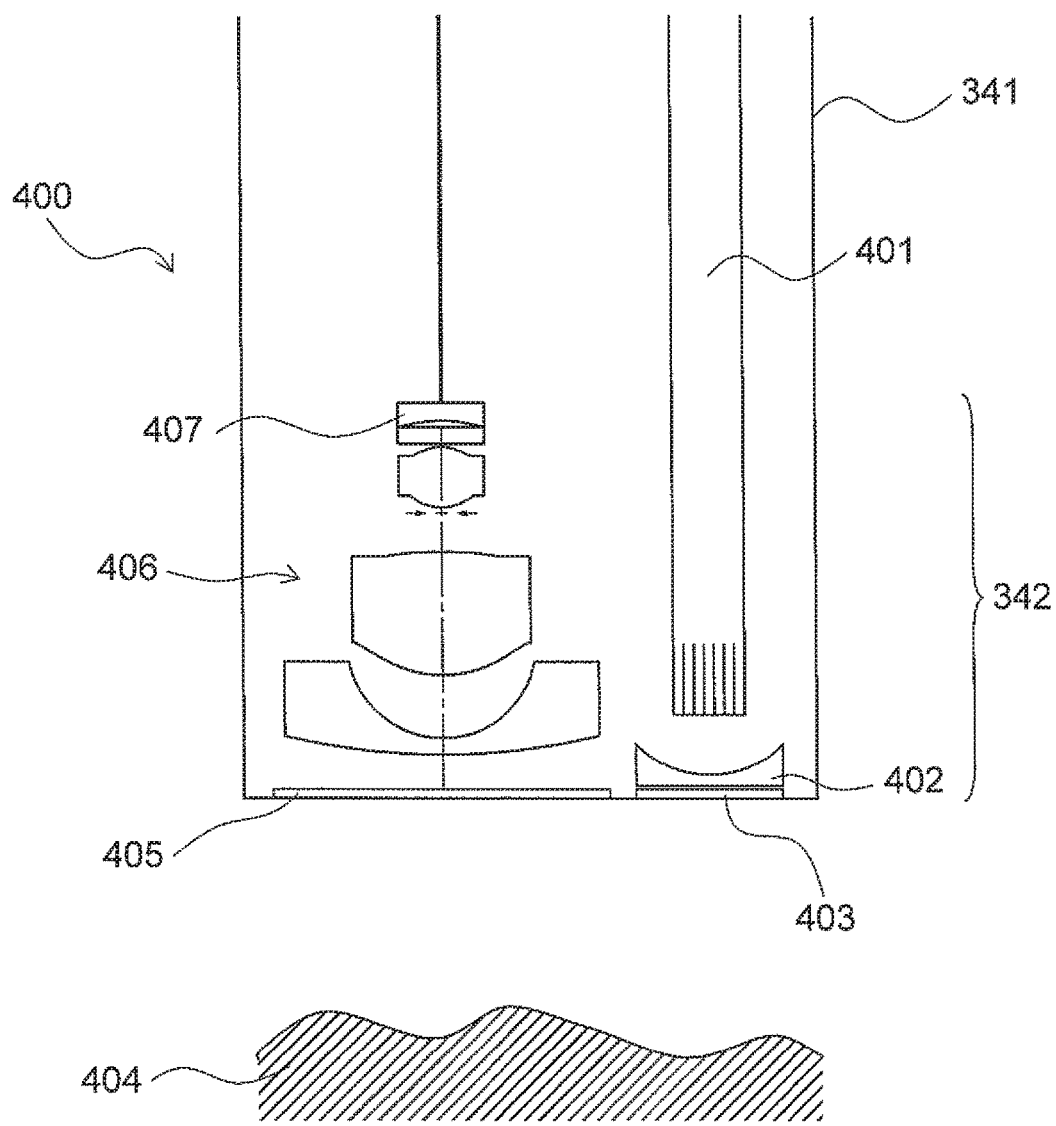
FIG. 9 is a diagram showing an arrangement of an optical system of an endoscope.

An optical system is disposed at a front-end portion 342 of the inserting portion 341. FIG. 9 is a diagram showing an arrangement of the optical system of the endoscope. An optical system 400 includes an illuminating section and an observation section.

The illuminating section includes a light guide 401 and an illumination lens 402. The light guide 401 transmits illumination light to a front-end portion 342 of an inserting portion 341. The illumination light transmitted emerges from a front-end surface of the light guide 401.

The illumination lens 402 is disposed at the front-end portion 342. The illumination lens 402 is disposed at a position facing a front-end surface of the light guide 401. The illumination light passes through the illumination lens 402, and emerges from an illumination window 403. Accordingly, a site to be observed inside a body to be examined (hereinafter, referred to as 'observation site 404') is illuminated.

In the front-end portion 342, an observation window 405 is provided adjacent to the illumination window 403. Light from the observation site 404 passes through the observation window 405, and is incident on the front-end portion 342. In a rear of the observation window 405, an observation section is provided.

The observation section includes an image forming optical system 406 and an image sensor 407. For the image forming optical system 406, the image forming optical system of the example 1 is used.

Light reflected from the observation site 404 passes through the image forming optical system 406, and is incident on the image sensor 407. An image (optical image) of the observation site 404 is formed on an image pickup surface of the image sensor 407. The image of the observation site 404 is subjected to opto-electric conversion, and accordingly, an image of the observation site 404 is acquired. The image of the observation site 404 is displayed on a display unit 330. In such manner, an observer can observe the image of the observation site 404.

In the image forming optical system 406, an image plane has a curved shape. The image sensor 407 has a light-receiving surface having a curved shape same as the shape of the image plane. By using the image sensor 407, it is possible to improve an image quality of a photographic image.

According to the present invention, it is possible to provide an image pickup apparatus which is capable of photographing a wide photographic range with a high resolution, while being small-sized.

As described above, the present embodiment is suitable for an image pickup apparatus which, while being small-sized, is capable of capturing a wide photographing range with a high resolution. Moreover, the present embodiment is suitable for an image pickup apparatus which includes an image forming optical system which, while being small-sized, has a wide angle of view and a small F-number, and is also capable of forming a favorable image.

What is claimed is:

1. An image pickup apparatus, comprising:
   an image forming optical system which includes an aperture stop that determines an axial light beam, and a plurality of lens components; and
   an image pickup section which is disposed on an image side of the image forming optical system, and has a light-receiving surface which is not flat and is curved to be concave toward the image forming optical system, wherein
   the lens component is a lens having only two surfaces in contact with air on an optical axis, which are, an object-side surface and an image-side surface, and
   the image forming optical system includes in order from an object side to an image side, a first lens component having a negative refractive power, a second lens component having a positive refractive power, and a third lens component having a positive refractive power, and
   a shape of the first lens component is a meniscus shape having a convex surface directed toward the object side, and
   a shape of the third lens component is a biconvex shape, and
   the following conditional expressions (1) and (2) are satisfied:

$$0.7 < |PS \times Rimg| < 1.5 \quad (1), \text{ and}$$

$$0.7 < |\theta out\, 90 / \theta img\, 90| < 1.5 \quad (2)$$

where,
   PS denotes Petzval sum for the image forming optical system, and
   Petzval sum PS is expressed by the following expression:

$$PS = \sum_{i=1}^{k} \frac{1}{n_i \times f_i}$$

where,
   i denotes an order of lens components from the object side in the image forming optical system,
   k denotes the total number of lens components in the image forming optical system,
   $n_i$ denotes a refractive index of an $i^{th}$ lens component for d-line,
   $f_i$ denotes a focal length of the $i^{th}$ lens component for d-line,
   Rimg denotes a radius of curvature of a virtual spherical surface including a surface apex and a point at which a chief ray incident on the image forming optical system at the maximum angle of view intersects the light-receiving surface, letting a point of intersection of the optical axis and the image-receiving surface to be the apex,
   θout 90 denotes an angle made by a predetermined chief ray emerged from an image-side surface of the third lens component and the optical axis,
   θimg 90 denotes an angle made by a straight line passing through two predetermined points and the optical axis, the predetermined chief ray is a chief ray for which an angle made with the optical axis becomes 90°, in a space on the object side of the first lens component, and the two predetermined points are a point of intersection of the predetermined chief ray emerged from the image-side surface of the third lens component and the virtual surface, and a center of curvature of the virtual surface.

2. The image pickup apparatus according to claim 1, wherein the aperture stop is disposed between a lens surface nearest to image of the second lens component and a lens surface nearest to object of the third lens component.

3. The image pickup apparatus according to claim 1, wherein the following conditional expression (3) is satisfied:

$$0.5<fL3/fL<3.4 \qquad (3)$$

where, fL3 denotes a focal length of the third lens component, and fL denotes a focal length of the image forming optical system.

4. The image pickup apparatus according to claim 1, wherein the following conditional expression (4) is satisfied:

$$1<(R1L+R1R)/(R1L-R1R)<2.5 \qquad (4)$$

where,

R1L denotes a paraxial radius of curvature of a lens surface nearest to object of the first lens component, and R1R denotes a paraxial radius of curvature of a lens surface nearest to image of the first lens component.

5. The image pickup apparatus according to claim 1, wherein the following conditional expression (5) is satisfied:

$$-2<(R2L+R2R)/(R2L-R2R)<0 \qquad (5)$$

where,

R2L denotes a paraxial radius of curvature of a lens surface nearest to object of the second lens component, and R2R denotes a paraxial radius of curvature of a lens surface nearest to image of the second lens component.

6. The image pickup apparatus according to claim 1, wherein the following conditional expression (6) is satisfied:

$$2.5<fL2/fL<8 \qquad (6)$$

Where, fL2 denotes a focal length of the second lens component, and fL denotes a focal length of the image forming optical system.

7. The image pickup apparatus according to claim 1, wherein each of the second lens component and the third lens component has an aspherical surface.

8. The image pickup apparatus according to claim 1, wherein each of the first lens component, the second lens component, and the third lens component is a single lens.

* * * * *